United States Patent [19]

Fahim

[11] 4,372,296
[45] Feb. 8, 1983

[54] TREATMENT OF ACNE AND SKIN DISORDERS AND COMPOSITIONS THEREFOR

[76] Inventor: Mostafa S. Fahim, 500 Hulen Dr., Columbia, Mo. 65201

[21] Appl. No.: 210,370

[22] Filed: Nov. 26, 1980

[51] Int. Cl.³ ............................................ A61H 23/00
[52] U.S. Cl. ................................. 128/24 A; 424/145; 424/166
[58] Field of Search ............................. 128/24 A, 1 R

[56] References Cited

PUBLICATIONS

Waters et al., Zinc-Sulfate-Failure as an Accelerator of Collagen Biosynthesis etc., Soc. for Ex Bio & Med. Proced., Oct. 1971, vol. 138, pp. 373-377.
Dilsen et al., Bohcet's Disease, Excerpta Medica, 1979, p. 301.
Graves et al., Hereditary Acrodermatitis Enteropathica in an Adult, Arch. Dermol., vol. 116, May 1980, pp. 562-563.
Pospisilor, A. J. et al., Acta Chirurgica Orthopaedicale et Traumatologiae Czech., vol. 35, Dec. 1968, pp. 478-483.
Elsias, L. J. et al., Inherited Human Collagen Deficiency: Ase Acid Response, J. of Pediatrics, vol. 92, No. 3, pp. 378-384.
Heughan, C. et al., Some Aspects of Wound Healing, Canadian Journal of Surgery, vol. 18, (2), 1975.
Fahim, Ser. No. 933,205, 8-14-78.

*Primary Examiner*—Kyle L. Howell
*Assistant Examiner*—Nancy A. B. Swisher
*Attorney, Agent, or Firm*—Grace J. Fishel

[57] ABSTRACT

A composition is disclosed which when topically applied is effective in the treatment of acne and skin disorders. While the etiology of the treatment is complex, it is believed that the composition reduces the rate of sebum secretion, inhibits the formation of keratin and fatty acids in the pilosebaceous ducts and is antimicrobial to the bacteria normally found in said ducts. The treatment is accomplished quicker and stimulates the production of collagen in the healing of scars if the composition is sonicated into the affected area with ultrasonic vibrations.

3 Claims, No Drawings

TREATMENT OF ACNE AND SKIN DISORDERS AND COMPOSITIONS THEREFOR

This invention relates to a composition for topical administration and to a method of treating acne and skin disorders.

Acne is a very common skin disease. It may be defined as a disorder characterized by seborrhea and obstruction of hair follicles with horny accumulations and is often complicated by the development of inflammatory lesions located on the face, neck, shoulders and chest, which include: (1) comedones, (2) whiteheads, (3) papules, (4) pustules, (5) cysts and (6) scars, i.e. (a) ice pick and shallow pock, (b) pits and (c) keloid and hypertropic.

Much work has been done in an attempt to understand the mechanisms of acnegenesis. An interaction between hormones, keratinization, sebum and bacteria somehow determine the course and severity of the disease. Attention has been paid in particular to the factors controlling sebaceous gland secretion and to the bacteriology of acne.

Acne begins at puberty, when an increase in androgens causes an increase in the size and activity of the pilosebaceous glands. In statistical terms acne patients have larger sebaceous glands and secrete more sebum than patients without acne probably because they have an enhanced response to circulating androgens. However, this does not necessarily apply to the individual since some greasy-skinned patients have no acne.

The sebaceous glands are small, sacculated, glandular organs lodged in the substance of the dermis. They are found in most parts of the skin, but are especially abundant in the face around the aperture of the nose and mouth. Each gland consists of a single duct more or less capacious, which emerges from a cluster of alveoli. Each alveolus is composed of a transparent basement membrane, enclosing a number of epithelial cells. The outer or marginal cells are continuous with the lining of the duct. The remainder of the alveolus is filled with larger cells, containing lipid, except in the center, where the cells become disintegrated leaving a cavity filled with their debris and with a mass of fatty matter, which constitutes the sebum. The ducts open most frequently into a hair follicle, but occasionally they open upon the surface of the skin as in the free margin of the lips.

When it emerges from the pilosebaceous duct, sebum contains triglycerides, waxes, squalene and fatty acids but as it emerges from the sebaceous gland it contains no fatty acids. While the sebum passes up the pilosebaceous duct, bacterial enzymes break down the triglycerides into free acid. The bacteria responsible for this are primarily *Corynebacterium acnes* and *Staphylococcus aureus*. Thus, the lipids which reach the skin contain not only triglycerides but free fatty acids. Some of the free acids are known to potentiate obstruction of the pilosebaceous duct.

Formation of an obstruction in the pilosebaceous duct is an essential step in the pathogenesis of acne. There are two types of obstructions, open comedones and closed comedones. A "blackhead" is an open comedo. With this type of obstruction, the contents of the sebaceous follicle can still escape to the surface and the pilosebaceous duct rarely becomes inflamed. In contrast, those lesions clinically classified as "whiteheads" are closed comedones. When the pilosebaceous duct is obstructed with a closed comedone, the sebaceous gland continues to excrete sebum. Bacteria present in the duct pour out lipases which, as aforementioned, break down the triglycerides into free acids which promote keratinization in the lamellae of the ducts. Eventually, the gland ruptures behind the blockage and liberates sebum into the dermis the most irritating component of which is the fatty acids.

In view of the above, it appears that an effective treatment for acne would reduce the occurrence of obstructions in the pilosebaceous duct if, among other things, it reduced the rate at which sebum is secreted and inhibited the formation of fatty acids in the pilosebaceous duct by reducing the microbiological flora therein. It is, therefore, an object of the present invention to provide a composition which is effective in the treatment of acne and skin disorders, particularly when applied with ultrasound, and which when applied with ultrasound reduces the sebum secretion rate, stimulates the production of collagen and has an antimicrobial effect on the bacteria in the pilosebaceous duct. Other objects and features will be in part apparent and in part pointed out hereinafter.

Many treatments for acne have been proposed in the past. Generally speaking, there have been topical methods of treatment, systemic and physical. None of these methods, it is believed however, are as effective or have the same mode of action as the present invention.

Other than for the present invention, topical treatments have involved the use of desquamative agents or antibacterial agents. The desquamative agents are supposed to work by unblocking the follicles. Sulfur in various concentrations is still one of the most widely prescribed agents in this category. Resorcin and beta-naphtol are also used in some peeling preparations. Benzoyl peroxide is available in some proprietary preparations but, as with sulfur, some individuals cannot tolerate the primary irritation that it causes. Abrasive agents have been used for desquamative agents as has retinoic acid. The mode of action for retinoic acid is uncertain but presumably it is related to the effect that vitamin A has at the glandular level.

Antibacterial agents are also used topically. These agents are employed in hope that they will reduce the local bacterial flora sufficiently to inhibit their hypothesized role in the lipolysis of the triglycerides in the sebum and thus prevent the liberation of fatty acids. In general, these agents are not very effective and they are in addition usually expensive and may be sensitizing.

Systemic treatments have relied on various antibiotics and sulfonamides, but the tetracyclines are the ones most widely used. While the tetracyclines have been used for many years, there is still controversy concerning their effectiveness and mode of action. There is a huge literature in which their use is described. Unfortunately, few of the published investigations were designed to produce an unbiased answer and the few that were well-constructed trials have yielded conflicting results. In any case, there is concern about administering systemic drugs since their use is at least potentially hazardous. For example, some women taking tetracycline develop vaginal yeast infection and tetracycline should not be given to pregnant women at all since it can cause deafness in the fetus.

Ultraviolet light has been used in the physical treatment of acne as have been X-rays. Surgery produces scars and does not aid in the resolution of the problem.

In general, the new compositions of the present invention contain a pharmaceutically acceptable, water soluble zinc salt and ascorbic acid. To be useful herein for the purposes of reducing the rate at which sebum is secreted and for reducing the number of bacteria in the pilosebaceous ducts, the zinc salt and the ascorbic acid are preferably present in an amount sufficient to provide a synergistic combination which has a greater than additive antimicrobial effect on the microflora found in the pilosebaceous ducts.

Insofar as known prior to the present discovery, it was not known that a combination of zinc ions and ascorbic acid would reduce the rate at which sebum is secreted and that if it was applied with ultrasonic vibrations that it would stimulate the production of collagen in the treatment of acne scars. Nor was it known that a combination of zinc ions and ascorbic acid could give rise to a synergistic combination useful in killing the normal microflora found in the pilosebaceous ducts.

The topical compositions of the present invention comprise a mixture of a pharmaceutically acceptable zinc salt and ascorbic acid. Suitable zinc salts include those zinc compounds which are soluble in water at body temperature and which are pharmaceutically acceptable. As such, they must have low human or animal toxicity when applied in the manner intended. Among the useful zinc salts are zinc sulfate monohydrate, zinc sulfate heptahydrate and the like. If the combination is to be stored, to prevent the oxidation of ascorbic acid, it is preferred that an antioxidant such as vitamin E be added. It is also preferred that vitamin A be added to smooth the skin.

In accordance with the present invention, the zinc salt and the ascorbic acid are preferably present in that amount sufficient to provide a synergistic combination effective as an antimicrobial agent against the microflora normally found in the pilosebaceous ducts, namely, effective against *Corynebacterium acnes* and *Staphylococcus aureus*. At that concentration, the composition will also be effective in the reduction of the sebum secretion rate and in the stimulation of collagen production. Excessive amounts of zinc or ascorbic acid beyond that necessary to provide an effective combination should be avoided since such amounts can cause skin irritation. As above mentioned, it is preferred that the composition include from about 50 to 500 IU/g of vitamin E, most preferably 100 IU/g, and from about 200 to 2000 IU/g of vitamin A, most preferably 1000 IU/g.

The zinc salt and ascorbic acid along with the vitamin E and vitamin A, if any, are mixed in a pharmaceutical carrier such as water, alcohol, glycerol, oils and mixtures thereof. It is important that the carrier be selected so that it does not inhibit the pharmacological activity of the zinc salt or the ascorbic acid. When the composition is sonicated into the affected area with ultrasonic vibrations, the carrier is preferably a coupling agent since ultrasound does not transmit through air.

Suitable coupling agents include mixtures of mineral oil and glycerine or the like but the preferred coupling agent is HEB cream sold by Barnes Hind Company. This material is a mixture of cetyl alcohol, stearyl alcohol, white petrolatum, mineral oil and propylene glycol.

When the zinc salt is zinc sulfate, an effective composition is prepared wherein the concentration of said salt is at least 0.5 percent by weight and wherein the ascorbic acid is present in a similar amount. The exact amounts can be adjusted depending on the effectiveness of the active ingredients such that an effective synergistic combination is obtained. Preferably, the zinc salt should be present in amount from 1 to 4 percent by weight while the ascorbic acid should be present in an amount from about 2 to 6 percent by weight. Higher concentrations are not preferred because they cause skin irritation.

One formula which is useful for patients who want a non-greasy, quick drying composition as, for example men with heavy beards, comprises 1 percent by weight of zinc sulfate and 4 percent by weight of ascorbic acid in an alcohol base. One such composition is formulated from 0.57 g zinc sulfate monohydrate U.S.P., 1.14 g ascorbic acid U.S.P., 1.0 g vitamin E (DL-α-tocopherol), 2.4 ml lemon extract, 2.25 g methyl cellulose, 50.0 ml Vehicle N and 1 drop of yellow food dye. Vehicle N is sold by Nutrogena Corporation and is a combination of ethyl alcohol, isopropyl alcohol, propylene glycol and purified water. In preparing the above-mentioned formulation, ascorbic acid, lemon extract and vitamin E are placed in a mortar and Vehicle N is added thereto. Methyl cellulose is then slowly added to make a thick gel. Zinc sulfate is dissolved in a small amount of water and then is incorporated into the gel. A drop of yellow food dye is added and mixed until an even color is achieved.

Another typical formula contains 1 percent zinc sulfate and 2 percent ascorbic acid and is useful for patients whose skin is irritated by a formula with an alcohol base. It is prepared from 0.6 g zinc sulfate monohydrate U.S.P., 1.12 g ascorbic acid, 48.0 g lubricating jelly, 2.4 ml lemon extract, 1 drop of yellow food coloring, 1.08 g methyl parabens, 0.27 g propyl parabens, 5.0 ml propylene glycol and 1.0 g vitamin E (DL-α-tocopherol).

The compositions of the present invention are made up by combining the zinc salt and ascorbic acid along with vitamin E and vitamin A, if present, with a pharmaceutical carrier in the amounts described above and by blending them until a substantially homogeneous mixture is formed. Since the composition is relatively shelf stable, particularly when an antioxidant like vitamin E is included, it may be prepared in advance and stored.

The compositions of the present invention are effective in the treatment of acne when they are applied to the skin whether or not they are sonicated into the skin with ultrasound. With ultrasound, however, they take effect quicker and can be used to stimulate the production of collagen in the healing of scars.

When the composition is applied with ultrasound, it is sonicated into the affected area with ultrasonic vibrations. The mode of action of this treatment is not fully understood but it is hypothesized that the ultrasonic vibrations may increase the permeability of the cells. The active components of the composition are otherwise substantially cell impermeable and they are thus effectively administered intracellularly with ultrasound.

When ultrasound is used, vibrations at a frequency in the range from 1,000 to 3,000 KHZ are preferred. Substantially lower frequencies are ineffective and higher frequencies should be avoided. The effective power level at the applicator head should be preferably in the range from 0.5 to 3.0 watts per sq. cm. In the treatment of scars, the ultrasound is preferably continuous and diffused over the area being treated, whereas in the treatment of acne it is preferably pulsed and finely focused to a point on the area undergoing treatment. The length of the treatment, output frequency and power level will vary in the individual case and is left to the physician.

Number and frequency of treatments is similarly left to the physician. If no ultrasound is used, a convenient regimen is for the patient to apply the composition once a day before going to bed. If ultrasound is used, treatments may be given daily at first for 2 to 3 minutes and then reduced in frequency or eliminated altogether when the desired effects are obtained. The patient can then administer the composition to himself like those patients who receive no ultrasound treatments in the beginning.

The following examples illustrate the invention:

EXAMPLE 1

An acne cream according to the present invention was prepared from the following ingredients:

| Zinc sulfate | 2% by weight |
|---|---|
| Ascorbic acid | 2% by weight |
| Vitamin A | 1250 IU/g |
| Vitamin E | 50 IU/g |
| In HEB cream | |

EXAMPLE 2

One hundred and eighty-six patients were treated for acne. The patients were classified clinically according to the grade of acne, i.e., mild, moderate or severe:

| Sex | Patients Treated for Acne | | | |
|---|---|---|---|---|
| | Average Age | Mild Acne | Moderate Acne | Severe Acne |
| 92 Males | 20.2 | 20 | 30 | 43 |
| 94 Females | 21.6 | 17 | 38 | 39 |

The following data was collected before and after treatment: percent of open comedones, percent closed comedones, percent of pustules, percent of erythema, distribution and photographs.

Patients with mild or moderate acne responded well to treatment with the acne cream described in Example 1, which involved application of the cream overnight, daily for 7 days, then every other day. In those patients with mild cases, nearly 100% of the acne lesions disappeared within 2 weeks; in those patients with moderate cases, 80% of the acne lesions disappeared within 8-10 weeks. It was noted that acne began to appear again 3 months after stopping the acne treatment but was controlled by continuous application every 3 days.

In patients with severe cases, there was no sign of improvement until after 3 months, and the indication was 50% improvement. However, when the cream was applied with ultrasound 3 times a week, 80% of the acne lesions disappeared after 6 weeks. In cases where the acne area is scarred, it is preferred if the cream be applied with a 10 sq. cm. applicator vibrating continuously at 1,000 to 3,000 KHZ at a power level of 0.5 watt/sq. cm. for 1 minute over each square inch area. However, when comedones are the most dominant lesion, a small 2 sq. cm. applicator is most effective having vibrations at 1000 to 3000 KHZ and a power level of 0.5 to 3.0 watts/sq. cm. with a pulse duration of 2 to 5 milliseconds and 10 to 15 milliseconds between pulses.

It was noted in come patients that their skin became dry and itching due to the action of zinc in the acne cream. To treat the dry, itching skin, a salve composed of 10% urea, 1000 IU vitamin A and 500 IU vitamin E in HEB cream was applied once a day in the morning. Itching stopped within 8 hours and the dryness disappeared within 5-7 days.

EXAMPLE 3

An acne cream according to the present invention was prepared by blending the following components:

| Zinc sulfate | 1% by weight |
|---|---|
| Ascorbic acid | 2% by weight |
| Vitamin E | 1000 IU/g |
| In HEB cream | |

EXAMPLE 4

It is known that acne in humans results from an increased rate of sebum secretion (Lancet 1:689, 1969; J. Investig. Dermatol. 43:387, 167) and it has been shown that the hormone, testosterone, will increase the rate of sebum secretion in rats (Proc. Royal Soc. Med. 62:49, 1969). The experiment in this example was conducted to show the effect of the acne cream prepared in Example 3 on the sebum secretion rate of male rats that had been treated with testosterone.

Forty male rates weighing 150+5 g were injected intraperitoneally with 3 mg of testosterone propionate daily for 30 days. Fifteen days after the testosterone injections were begun, the animals were divided into four groups. Group I was the control. The rats in Group II were treated with ultrasound by placing the rate in a 300 ml water bath with an ultrasonic applicator immersed at the bottom of the bath. The ultrasonic applicator was connected to an ultrasonic generator vibrating at a frequency of 1,000 KHZ and the power level at the applicator head was 1 watt per sq. cm. The rats were treated in the bath for 5 minutes on seven occasions, one every other day for two weeks.

The rats in Group III were treated with 2.0 g of the acne cream described in Example 3 once a day for 15 days and the rats in Group IV were treated with acne cream like those in Group III and with ultrasound like those in Group II.

The sebum secretion rate was measured 30 days after the testosterone injections were started using the Archibald method (Br. J. Dermatol. 82:146, 1970). Measurements were made on four consecutive days and are reported in the following table:

| Total Sebum Secretion Rate During 4 days | |
|---|---|
| Group | Mg sebum/g body weight |
| I | 14.6 ± 0.3 |
| II | 13.9 ± 0.8 |
| III | 11.3 ± 0.6 |
| IV | 7.1 ± 0.4 |

The above results indicate that the acne cream of the present invention particularly when applied with ultrasonic vibrations, decreases the sebum secretion rate of testosterone-treated rats.

EXAMPLE 5

In this example, acne was induced in the external ear canal of rabbits and then was treated with the acne cream described in Example 3. More particularly, 5.0 mg testosterone propionate was injected subcutaneously into the ear canal of 15 young adult albino rabbits weighing 6.2±0.2 pounds. One ear was treated, the other served as a control. Unlike human sebaceous glands which are located on one side of a hair bearing follicle, the sebaceous glands in rabbits consist of many small acini circumferentially distributed around the hair bearing portion of the follicle. Each acinus has a duct which fuses with neighboring sebaceous ducts before emptying into the follicular canal. In rabbits, as in humans, the pilosebaceous duct contains concentric lamellae of keratin and obstruction of the duct is in part due to the increase in the amount and the rate at which keratin is formed.

Before treatment with the acne cream, whole glycerin mounts were prepared by Hambrick's technique (J. Investig. Dermatol. 28:89, 1957) from tissue excised from the ears of each rabbit ten days after the testosterone injection. The follicles were marked by thickened mounds which indicated distension and obstruction by horny material. The rabbits were then divided into three groups for further testing.

The rabbits in Group I were treated with ultrasound. The applicator was coupled to an ultrasound generator which vibrated at a frequency of 1,000 KHZ and the power level at the applicator head was 0.5 watt per sq. cm. HEB cream was used as the coupling agent and the ultrasound treatment was applied for 5 min. every other day.

The rabbits in Group II were treated with 2.0 g of the acne cream described in Example 3 once a day and the rabbits in Group II followed by an ultrasound treatment every other day as were those in Group I.

After two weeks of treatment, an ellipse of tissue about one-half inch long was excised from both ears of each rabbit, fixed in formaldehyde and stained with hematoxylin and eosin. Horizontal sections were taken because all of the follicles could be visualized in a single cut. Four slides were adequate to document the condition of the follicles from top to bottom. Histological examination of these sections revealed that the rabbits in Group I had significant hyperkeratosis, those in Group II showed reduced hyperkeratosis while those in Group III showed normal keratinization so that the tissue from the treated ears was like the tissue from that of the control ears.

EXAMPLE 6

In this example, zinc sulfate and ascorbic acid were each checked for its effectiveness on the growth of *Corynebacterium acnes* in vitro. This bacterium, as mentioned above, is present in the pilosebaceous ducts and is implicated in acnegenesis. A synergistic combination of zinc sulfate and ascorbic acid was then prepared and its effectiveness checked. The results were reported in the following table.

| Trial | Growth of Corynebacterium acnes in vitro | | | | | | | | | |
|---|---|---|---|---|---|---|---|---|---|---|
|  | 1 | 2 | 3 | 4 | 5 | 6 | 7 | 8 | 9 | 10 |
| 1% $ZnSO_4.7H_2O$ | M* | M | M | M | S* | M | S | M | M | M |
| 1% Ascorbic acid | M | M | M | S | M | S | S | M | M | S |
| 1% $ZnSO_4.7H_2O$ + Ascorbic acid | NG* | NG | NG | NG | NG | NG | NG | NG | NG | NG |

*M = moderate growth
S = scant growth
NG = no growth

In view of the above, it will be seen that the several objects of the invention are achieved and other advantageous results attained. As various changes could be made in the above-mentioned methods and compositions without departing from the scope of the invention, it is intended that all matter contained in the above description shall be interpreted as illustrative and not in a limiting sense. The invention accordingly comprises the methods and compositions hereinbefore described, the scope of the invention being indicated by the subjoined claims.

What is claimed is:

1. A method for treating acne comprising topically administering with ultrasonic vibrations at a frequency between 1000 KHZ and 3000 KHZ and at a power level between 0.5 and 3.0 watts per sq. cm. to acne affected skin an effective amount of a composition comprising from about 1.0 to about 4.0 percent by weight of zinc sulfate and from about 2.0 to about 6.0 percent by weight of ascorbic acid in a pharmaceutical carrier which is an effective coupling agent for ultrasonic vibrations and which does not inactivate the pharmacological activity of the zinc salt or ascorbic acid whereby said composition effectively retards the rate of sebum secretion in the treated area and stimulates the production of collagen.

2. The method of claim 1 wherein the ultrasonic vibrations are pulsed and finely focused on the acne affected skin being treated.

3. The method of claim 1 wherein the ultrasonic vibrations are continuous and diffusely focused on the acne affected skin being treated.

* * * * *